US009374397B2

(12) United States Patent
Platt et al.

(10) Patent No.: US 9,374,397 B2
(45) Date of Patent: Jun. 21, 2016

(54) METHOD AND SYSTEM FOR SEARCHING, SENSING, DISCOVERING, SCREENING, ENABLING AWARENESS, ALERTING, SHARING, SENDING, RECEIVING, BUYING, SELLING, AND OTHERWISE TRANSMITTING STORIES, CONTENT, INTERESTS, DATA, GOODS AND SERVICES AMONG KNOWN AND UNKNOWN DEVICES IN A COMMUNICATION NETWORK

(71) Applicants: Timo Platt, North Hampton, NH (US); Stephan Krueger, Salem, NH (US); Barbara Roselle, Andover, MA (US)

(72) Inventors: Timo Platt, North Hampton, NH (US); Stephan Krueger, Salem, NH (US); Barbara Roselle, Andover, MA (US)

(73) Assignee: Pokos Communications Corp, Portsmouth, NH (US)

( * ) Notice: Subject to any disclaimer, the term of this patent is extended or adjusted under 35 U.S.C. 154(b) by 341 days.

(21) Appl. No.: 13/870,456

(22) Filed: Apr. 25, 2013

(65) Prior Publication Data

US 2013/0311562 A1    Nov. 21, 2013

Related U.S. Application Data

(60) Provisional application No. 61/648,212, filed on May 17, 2012.

(51) Int. Cl.
*G06F 15/16* (2006.01)
*G06F 15/173* (2006.01)
(Continued)

(52) U.S. Cl.
CPC .............. *H04L 65/403* (2013.01); *G06Q 30/02* (2013.01); *G06Q 30/0256* (2013.01); *H04L 67/18* (2013.01); *H04W 4/02* (2013.01)

(58) Field of Classification Search
CPC ........... G06Q 30/0269; G06Q 30/0261; H04L 67/18; H04L 67/306
USPC ......................................... 709/224, 218, 228
See application file for complete search history.

(56) References Cited

U.S. PATENT DOCUMENTS 8,284,748 B2    10/2012    Borghei
8,384,684 B2    2/2013     Westerman
(Continued)

OTHER PUBLICATIONS

Heinemann, Collaboration in Opportunistic Networks, 2007.*
(Continued)

*Primary Examiner* — Hieu Hoang

(57) ABSTRACT

Systems, method and apparatus are provided for searching, sensing, discovering, screening, enabling awareness, alerting, sharing, sending, receiving, buying, selling, and otherwise transmitting stories, content, interests, data, goods and services among known and unknown devices in a communication network. Humans have a core desire to communicate and share with those around them—both nearby and around the globe—to enhance their individual, social and shared experiences. Social networks and related technologies have provided their subscribers with new technologies to share their stories with their friends and certain third-parties, but are limited in two crucial respects: they require prior membership, subscription or enrollment; and, in order to execute communications with friends and certain third parties, social networks require use of both (a) a user's existing contact information, and (b) the social network's platform. By using improved methods for searching, detecting, sensing, and discovering attributes, characteristics, parameters and other data between devices among known and unknown devices, then people, businesses and organizations will be able to sense, learn and act on the interests, attributes, stories, content and products of others, enabling enhanced forms of communications and new methods of business.

6 Claims, 1 Drawing Sheet

(51) Int. Cl.
  *H04L 29/06* (2006.01)
  *G06Q 30/02* (2012.01)
  *H04W 4/02* (2009.01)
  *H04L 29/08* (2006.01)

(56) References Cited

U.S. PATENT DOCUMENTS

| | | |
|---|---|---|
| 8,385,039 B2 | 2/2013 | Rothkopf |
| 8,401,009 B1 | 3/2013 | Dorsey et al. |
| 8,417,575 B2 | 4/2013 | Nakajima et al. |
| 8,417,779 B2 | 4/2013 | Weber |
| 2007/0271518 A1 | 11/2007 | Frank et al. |
| 2010/0112989 A1 | 5/2010 | Andreasson |
| 2013/0099892 A1 | 4/2013 | Tucker et al. |
| 2013/0103200 A1 | 4/2013 | Tucker et al. |

OTHER PUBLICATIONS

Andreas Heinemann, Collaboration in Opportunistic Networks (VDM Verlag 2007) (dissertation, Darmstadt University of Technology, Germany).

WiFi Alliance, "Wi-Fi Aware™: Discover the World Nearby, Enabling Personalized Social, Local, and Mobile Experiences" (Jul. 2015 Austin, Texas, USA).

WiFi Alliance, "Neighbor Awareness Networking, Technical Specification, Version 1.0" copyright 2015 (Austin, Texas).

* cited by examiner

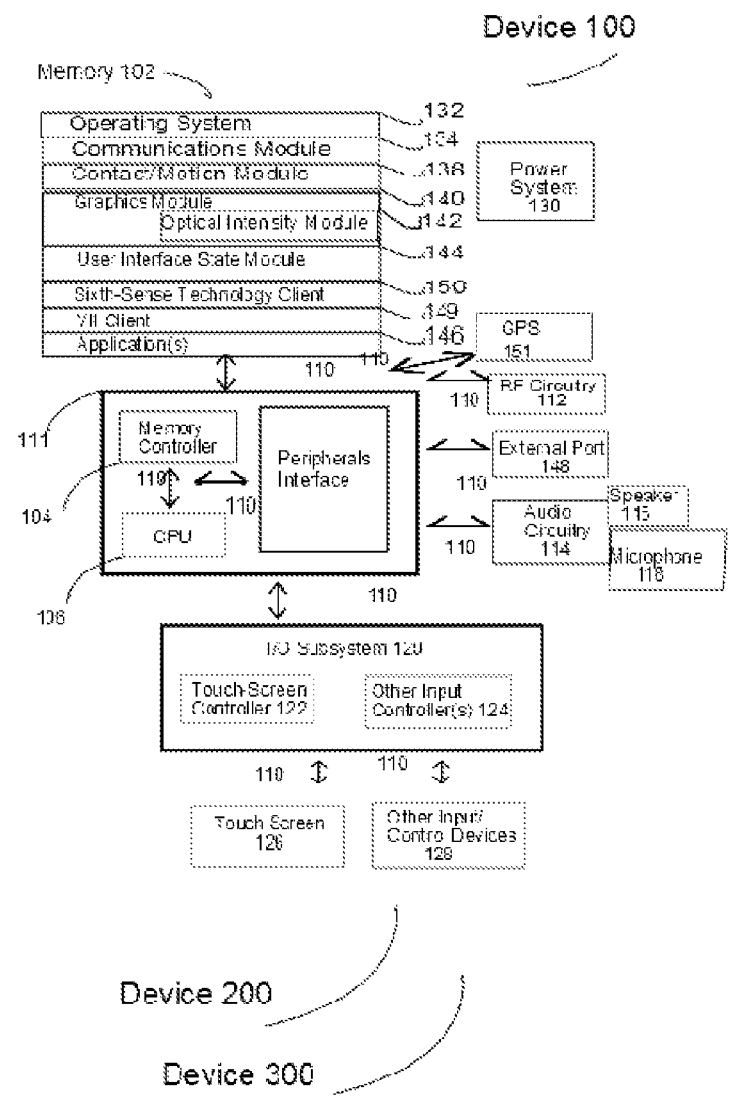

METHOD AND SYSTEM FOR SEARCHING, SENSING, DISCOVERING, SCREENING, ENABLING AWARENESS, ALERTING, SHARING, SENDING, RECEIVING, BUYING, SELLING, AND OTHERWISE TRANSMITTING STORIES, CONTENT, INTERESTS, DATA, GOODS AND SERVICES AMONG KNOWN AND UNKNOWN DEVICES IN A COMMUNICATION NETWORK

TRANSITION APPLICATION: CROSS-REFERENCE TO RELATED APPLICATIONS

This application is a transition application under the America Invents Act (AIA), insofar as it claims priority to or the benefit of the filing date of the following described provisional application filed prior to Mar. 16, 2013; specifically it claims benefit under 35 U.S.C. 119(e) of U.S. Provisional Patent Application No. 61/648,212, entitled, "Communication Methods between, among and to both Known and Unknown Devices for Searching, Sending and Receiving Voice, Video and Data and Creating Sixth-Sense Technologies and Discovery Engine for Sensing, Becoming Aware of, Sharing and Learning Stories, other Content, Interests and data of all kinds", filed May 17, 2012, which is incorporated herein in its entirety.

INCORPORATION BY REFERENCE: CROSS-REFERENCE TO RELATED PRIOR ART

The invention and technology described in this application improve on, extend, enlarge and create new processes relating to, and perhaps in part foreseeable from, the prior art described in the following patents, U.S. Pat. No. 8,396,489, entitled, "Method and System for Transmitting and Receiving Messages", issued Mar. 12, 2013, and U.S. Pat. No. 8,396,490, entitled "Method and System for Transmitting and Receiving Messages", issued Mar. 12, 2013 (such applications jointly herein, the "Prior Patents"), which were filed by and on behalf of two of the within Inventors (Platt and Krueger), and their colleague Mr. Kevin King, as assigned to their affiliate company, PoKos Communications Corp (the inventions claimed by the Prior Patents collectively herein, the "Related Inventions")—which is also the assignee of the within application. This application incorporates by reference the Prior Patents.

FIELD OF THE DISCLOSURE

This disclosure relates generally to a method and system for searching, sensing, discovering, screening, enabling awareness, alerting, sharing, sending, receiving, buying, selling, and otherwise transmitting stories, content, interests, data, goods and services among known and unknown devices in a communication network.

BACKGROUND

Humans have a core desire to communicate and share with those around them—both nearby and around the globe—to enhance their individual, social and shared experiences. Since the beginning of recorded history, they have told stories to connect them with their past and with each other, and to improve their understanding and enjoyment of life. (In this Application, we use the term "stories" not only in the dictionary sense of 'text-based narrative' but also stories told via the visual arts, pictures, movies, music, messaging, social media, etc, and whether by voice, video, data or multi-media.)

Stories have or will become a metaphorical sixth sense, adding both a personal and a social sense to the traditional five personal senses (touch, sight, hearing, smell, taste).

Because stories bring people together—in person, as well as intellectually, emotionally, psychologically, spiritually, and socially—and enhance understanding, humans have an implicit yearning to sense what others are thinking, or 'get inside their thought bubble'. When meeting someone for the first time, or confronting an adversary or a new way of thinking, a typical human response is to the effect of "what's their story?" Humans want to be able to sense it, to understand it.

Social networking, social media and other recent interactive software applications and media (collectively herein, "social networks") have provided their subscribers with new technologies to share their stories with their friends and certain third-parties, but are limited in two crucial respects: they require prior membership, subscription or enrollment; and, in order to execute communications with friends and certain third parties, social networks require use of both (a) a user's existing contact information, and (b) the social network's platform. Except for the art described and claimed in the Prior Patents, the prior art, up to and including sharing through social networks, is based on the premise that directed private communications are only possible or feasible between, among and to known fixed endpoints.

Typically, a phone number, address, or login information ("traditional identification information") is needed to initiate a communication with a specific person. For example:
(1) to call a person, you dial a phone number;
(2) to text a person, you need their mobile phone number;
(3) to send an instant message, you need their email address, or a specific screen name or alias registered with the maker of an instant messaging application (e.g., Google Talk; AOL AIM);
(4) to email a person, you need an email address; and
(5) for web-based or mobile social networks, sites, or applications (jointly, "Social Medium"), you need to: (a) register with a specific Social Medium, providing either your email address or phone number; and (b) know or have access to a user's name or login information to communicate with them.

However, there are many situations where this traditional identification information is not known, but individuals still wish to communicate with others whose traditional identification information they do not know.

Further, social networks and other Social Media are by their very nature self-limiting: s/he is either a member or one is not. If one is a member of a specific Social Medium, then s/he enjoys the benefits of that network. Non-members cannot receive the network's benefits. Our sixth-sense technology invention, by contrast, conceives a communications globe where everyone, every device and every server is connected, as part of a universal communications field—and is thus more akin to the earth's magnetic field and gravitational force, making continuous connections with others, as if sharing brain waves or even spiritual connections.

As a further distinction from the prior art, our sixth-sense technology gives users complete control of inbound and outbound communications, for everything from privacy and anonymity to depth and breadth of the content s/he shares. In this context, user communications are very personal, and infinitely variable. From this perspective, user communications are unstructured both in theory and in fact. By contrast, social networks impose a set of structured rules for member participation, and frequently dictate an inverse correlation between privacy and breadth of communication.

Our SST inventions overcome these limitations by enabling the sharing of stories, privately and anonymously, without reliance on or use of traditional contact information, third-party platforms, functionalities, or capabilities. All aspects of storing-telling—'sensing', discovery, searching, becoming aware, sharing, learning, sending, transmission and receiving functions—can all be performed as an inherent part of the communications process and communications operation, using the technologies of our invention embedded in their communications devices and/or in the associated enhanced communications network(s).

Our sixth-sense communications technology will enable users to search, send and receive voice, video and data between, among and to devices that are unknown to the sender or recipients (such devices herein "unknown devices"). Users will use the invention to sense what others want or are willing to share and learn, and thus share their stories and interests with others around them and around the globe. Our communications invention will power the discovery and delivery of all forms of global content and commerce.

Our invention and technology enable this new communications method, through:
(a) new processes to search, detect, discover, alert and sense unknown recipients and their unknown devices with attributes (i) lying within specified parameters, (ii) having common, variable or random characteristics, or (iii) determined by algorithm or otherwise,
(b) use new processes to enable a device user and others to direct a targeted message, voice, video, data or other communication to the unknown recipients on their unknown devices,
(c) through the combination of such processes in steps (a)-(b) above, to launch a new era of sixth-sense communications that enable people to "sense" and be alerted of others with whom they want or are willing to communicate and then act on that sense to share and learn their respective stories and interests, thus creating new ties that bond and bring people together, and
(d) through the combination of such processes in steps (a)-(c) above, to enable the discovery, alerting, and delivery of all forms (e.g., voice, video, data, multi-media) of global content and commerce among devices and people based on such sixth-sense communications capabilities (the methods and processes referred to in steps (a)-(d) above collectively herein, "Communications Methods", and the Inventions covered hereby "Sixth-Sense Technology", or simply "SST").

People will thus use their communications devices embedded with our invention to "sense" and become aware of others—whether a new schoolmate, someone across town, or unknown individuals and groups halfway around the globe—with whom they want or are willing to communicate and then act on that sense to share and learn their respective stories and interests.

Our SST invention will thus bestow people with an artificial sixth sense—simply by using their communications devices—for them to search, sense, detect, be alerted, tell, and learn from the sharing of stories with others.

With the exception of what is contemplated by and/or foreseeable from the Related Inventions and the Prior Patents, we are not aware of anything in the prior art that heralds these new inventions and capabilities covered by this patent application.

SUMMARY

For wired, wireless and other communications, we have conceived, created and developed new communications methods for people, businesses and organizations ("participants") to search, sense and become aware of what others are interested in (and/or with whom they want or are willing to communicate) and to connect those people in private and anonymous communications based on their shared interests and thoughts.

A shorthand description of this new invention is as follows:
(a) it performs a search/discovery engine function in the fields of communications, thoughts and interests, similar to the following familiar tools: what an Internet search engine does for URL addresses and content; what a telephone directory does for phone numbers; what a television guide does for broadcast and cable television;
(b) it enables sensing, alerting, and becoming aware of such other persons and/or devices;
(c) it enables the delivery and completion of the sender's communications and stories, privately and anonymously, with unknown recipients and devices selected by the sender; and
(d) the sixth sense discovery invention performs both "push" and "pull" functions.

One aspect of the present SST invention relates to creating and providing people with the ability to search, "sense" and be alerted to unknown third parties with whom they want or are willing to communicate ("recipients"), and engage directly in real-time communications with such unknown recipients, without knowing the identity, address, contact information or location of the recipients (herein, "unknown recipients").

Another aspect of the present SST invention also relates to creating and providing people with the ability to search, sense and be alerted to what others are interested in (and/or with whom they want or are willing to communicate) and to connect those people in private (or public) and anonymous communications based on their shared interests and thoughts.

Another aspect of the present SST invention also relates to creating and providing participants, groups, businesses, organizations and other parties with the means to search, discover and be alerted to what other people are interested in, and to deliver, share and learn to, with and from new and unknown recipients, through the exchange of voice, video, data and multi-media.

A first embodiment—of the single or multi-user push operation for our sixth-sense discovery invention—relates to creating and providing people with the ability to send real-time content to one or more others who might be interested in a particular topic. An example of this embodiment is where a person or organization wants to direct in real-time content (e.g., in the form of a message or voice alert) to one or more others who might be interested in a particular political or social cause. The person or organization would use a device and communications network enhanced by the invention to discover and become aware of who is interested in receiving such content, and then send the desired content, privately and anonymously, to all unknown recipients chosen by the sender.

A second embodiment—of the single or multi-user pull operation of our sixth-sense discovery invention—relates to creating and providing people with the ability to learn more about a particular topic. An example of this embodiment is where a person wants to learn more about "gay marriage". While attending a business conference, his device (enhanced with our invention) senses that a gay rights activist is nearby, and sends him an alert. The participant checks his device; learns that Lloyd C. Blankfein, the chief of Goldman Sachs and national corporate spokesperson for The Human Rights Campaign (THRC), is sitting across the aisle; texts Mr. Blankfein to set up an inquiry or even a meet and greet; and then at Mr. Blankfein's request, receives a full report from THRC reviewing both sides of the gay marriage debate.

A third embodiment relates to creating and providing new communications methods for people, groups, businesses, organizations and other parties to search, discover and become aware of what other people are interested in, and to deliver, share and learn, with and from new and unknown recipients, through the exchange of voice, video, data and multi-media. An example of this embodiment is where a person desires to find out what interests others, inclusive of everyone from the newcomer at school, the person across town, or someone halfway around the globe. People will get a sense of and be alerted to the other guy's 'story', and be able to share voice, pictures, video and data content based on common interests, creating ties that bind, and bringing people together.

A fourth embodiment relates to creating and providing businesses and people, and governments, institutions, and other organizations, with:
  new methods for searching and prospecting for new customers and contacts,
  new methods for distributing and selling new and additional products to existing and new customers,
  new methods for conducting market research, consumer surveys, surveys and focus groups for new product features, new products, product development, and research and development,
  new methods for forecasting demand and creating, maintaining and improving operations and supply-chain management, and
  new methods for conducting global, supra-national, national, regional and census, public health and other data-gathering; public policy development; dissemination of emergency alerts, public-health news and other information; distribution of benefits; and political outreach, recruitment, opinion polls, advocacy and other political activities.

An example of this embodiment is where a businesses or organization wants to discover, become aware of, and/or engage new customers and prospects for their products, services and causes. Another example of this embodiment is where a media content producer would use our new communications methods to discover and become aware of which groups of anonymous consumers are or might be interested in their content; send those people a message or alert that their content is available for purchase, streaming or download; and then complete the delivery of their content to such unknown people or devices—without needing to negotiate with a cable television company or other digital distributor, for example, terms and conditions, including without limitation such terms as: bundled-service package restrictions and/or other conditions; distribution fees and/or transaction commissions or fees; or digital rights management restrictions. Freed of such restrictions and costs, vendors will receive the following benefits:
  (i) greater adjusted gross margins, which enable both lower consumer prices and greater business reinvestment;
  (ii) by gaining direct access to customers and prospects: (a) new ideas for new products, features, and improvements to existing products, and (b) greater customer satisfaction and loyalty;
  (iii) lower costs resulting from reduced license fees and similar expenses relating to license/rental of third-party 'house lists' and other prospecting databases; and
  (iv) other benefits resulting from avoidance of competitive restrictions dictated by third parties who control access to the customer and prospect of the vendor's products, services and/or causes.

A fifth embodiment relates to creating and providing consumers with new methods for purchasing products or services. An example of this embodiment is where an individual wants to remain anonymous throughout the entire purchase process, from research and screening, to referrals and recommendations, to closing the deal. Another example of our searching, sensing, discovery, alerting, and delivery method is where a novice consumer wants to start a reggae musical collection, so she uses our new communications method to identify an industry expert, solicit and procure their recommendations, and purchase selected digital music directly from the artists' mobile website, all privately and anonymously—without needing: (i) an account; (ii) membership for distributors like iTunes or Spotify; or (iii) searches of websites or Internet URLs.

In some embodiments, a method is disclosed of selectively communicating with one or more other devices whose identification information is unknown, the method comprising launching a client application on a device, wherein the client application enables communication with other devices whose identification information is unknown, identifying and locating other devices listing a searched-for identified attribute (such as at least one of the user's professional, associational, personal, physical, social, athletic, recreational, hobby and other interests and attributes), or any other data associated with the device or its user, that the second client application compiles; obtaining information regarding the other devices listing such searched-for attribute; compiling the information regarding the other devices listing the searched-for attribute to enable selection of at least one device to initiate communication using service messages, tags or tokens or other identifiers (jointly herein, "Variable Identifiers"); displaying a selection of the at least one device from the compiled information of the other devices listing such searched-for attribute; enabling privacy preferences for the device, wherein the privacy preferences enable the device to provide variable identification information to the at least one other device; enabling the client application on the device to specify whether the Variable Identifier is associated with private content, wherein the private content is sent only to the at least one other device; and sending the private content from the device to the at least one other device.

In some embodiments, a method is disclosed of selectively communicating with one or more other devices whose identification information is unknown, the method comprising launching a client application on a device, wherein the client application enables communication with other devices whose identification information is unknown; identifying an attribute (such as at least one of the user's gender, professional, associational, personal, physical, social, athletic, recreational, hobby and other interests and attributes), or any other data associated with the device or its user, that the device or its user wants to make known to other devices and users whose identification is unknown, which attribute is compiled by the first client application; identifying at least one criterion (such as attribute, location, time of day, date, etc) for sharing such attribute with at least one other user or device, which criterion is compiled by the first client application; identifying and locating other devices based on such one or more criteria; obtaining information regarding the other devices meeting such criteria; compiling the information regarding the other devices meeting such criteria to enable selection of at least one device to initiate communication using service messages, tags or tokens or other identifiers (jointly herein, "Variable Identifiers"); displaying a selection of the at least one device from the compiled information of the other devices meeting such criteria; enabling privacy preferences for the device, wherein the privacy preferences enable the device to provide variable identification information to the at least one other device; enabling the client application on the device to specify whether the Variable Identifier is associated with private content, wherein the private content is sent only to the at least one other device; and sending the private content from the device to the at least one other device.

In some embodiments, a method is disclosed of selectively communicating with one or more other devices whose identification information is unknown, the method comprising launching a client application on a device, wherein the client application enables communication with other devices whose identification information is unknown; identifying the other devices based on selected criteria using the client application, wherein the selected criteria comprise both (i) a searched-for identified attribute (such as at least one of the user's professional, associational, personal, physical, social, athletic, recreational, hobby and other interests and attributes), or any other data associated with the device or its user, and (ii) one or more searched-for locations or zones (jointly herein, a "zone"); obtaining attribute and/or other data and information regarding the other devices located in the searched-for zone; compiling such information regarding the other devices located in the searched-for zone to enable selection of at least one device to initiate communication using service messages; displaying a selection of the at least one device from the compiled information of the other devices located in the searched-for zone; enabling privacy preferences for the device, wherein the privacy preferences enable the device to provide variable identification information to the at least one other device; enabling the client application on the device to specify whether the Variable Identifier is associated with private content, wherein the private content is sent only to the at least one other device; and sending the private content from the device to the at least one other device.

In some embodiments, a device for selectively communicating with one or more other devices whose identification information is unknown, the device comprising an interface that is configured to communicate with the one or more other devices, and a client application that is configured to communicate with the interface to search for at least one of the one or more other devices based on selected criteria specified in the client application and to compile information obtained from the one or more other devices; the client application further configured to send a message to one or more other devices selected from the compiled information, and to enable privacy preferences for the device, wherein the privacy preferences enable the device to provide variable identification information to the at least one other device, as well as to enable the client application to specify whether the variable identification information is associated with private content, so that the private content is sent only to the at least one other device; and the device interface configured to send the private content from the device to the at least one other device.

In some embodiments, a method of selectively communicating between devices when identification information used to contact a device is unknown, the method comprising receiving, at a remote processing server, registration information from a first device; creating user identification information for the first device and associating the user identification information with the registration information; determining attributes and criteria for the first device and associating the criteria in the database with the user identification information of the first device; receiving, at the remote processing server, a second registration from at least one other device; organizing information from the first device and the at least one other device in a database on the remote processing server; determining attributes and criteria for the at least one other device and storing in the database; receiving a service message, at the remote processing server, from the first device, wherein the service message comprises content and user identification information; searching the database using the criteria selected by the first device to locate at least one other device that is within parameters specified by the first device; obtaining information for the at least one other device and processing the service message to send to the at least one other device; and sending a processed service message including the content of the service message to the at least one other device.

BRIEF DESCRIPTION OF THE DRAWINGS

FIG. 1 illustrates communications devices that provide searching, discovering, sensing, sharing, sending and receiving stories, content, interests and data among known and unknown people and devices, including communication to and with recipients whose traditional identification information is unknown in accordance with certain embodiments.

A method and system for searching, sensing, discovering, enabling awareness, alerting, screening, sharing, sending, receiving, buying, selling, and otherwise transmitting stories, content, interests, data, goods and services among known and unknown devices in a communication network.

DETAILED DESCRIPTION

Methods and systems are provided for searching, sensing, discovering, sharing, sending and receiving stories, content, interests and data among known and unknown people and devices in a communication network, in accordance with certain embodiments.

Platt et als teach us how to communicate without traditional identification information or communication methods, both directly between devices, U.S. Pat. No. 8,396,489, and with the aid of a server, U.S. Pat. No. 8,396,490 (the "Related Inventions").

But the Related Inventions do not teach how to search, discover, sense, share, send and receive stories, content, interests and data among known and unknown people and devices. For example, you may want to "know the story" of, or learn something about, an unknown person across the street, across the stadium, or on the other side of the world—without sending a message and awaiting a response. Another example is where you may want to purchase a new product or service, but don't know a business that sells it—and you don't have access to the Internet or don't have the time to conduct a web search. Another instance could be where business may want to find new customers or prospects—without renting or buying a list of names. A different example could be where an artist or producer may want to distribute its artistic creation—without using a digital distributor like Comcast or iTunes. In order to provide this type of communication among and with people, groups, and devices whose traditional identification information is unknown, various systems, methods, and apparatus are disclosed.

Reference will now be made in detail to embodiments, an example of which is illustrated in the accompanying drawing. In the following detailed description, numerous specific details are set forth in order to provide a thorough understanding of the present invention. However, it will be apparent to one of ordinary skill in the art that the present invention may be practiced without these specific details. In other instances, methods, procedures, components, and circuits taught by the Related Inventions—for both (a) communications without traditional identification information, and (b) communication methods, both directly between devices and with the aid of a server—have not been described in detail so as not to unnecessarily obscure aspects of the embodiments.

FIG. 1 illustrates communications devices that provide searching, discovering, sensing, sharing, sending and receiving stories, content, interests and data among known and unknown people and devices, including communication to and with recipients whose traditional identification information is unknown in accordance with certain embodiments.

FIG. 1 illustrates a portable, mobile or static-location electronic device, according to some embodiments of the invention, including, by way of illustration and not limitation, a server, router, switch, personal computer, laptop, notebook, mobile devices such as a tablet, smartphone, and wearable computers such as shoes, glasses, or implanted chips. The device 100 includes a memory 102, a memory controller 104, one or more processing units (CPU's) 106, a peripherals interface 108, RF circuitry 112, audio circuitry 114, a speaker 116, a microphone 118, an input/output (I/O) subsystem 120, a touch screen 126, other input or control devices 128, and an external port 148. These components communicate over the one or more communication buses or signal lines 110. The device 100 can be any electronic device, including but not limited to a desktop or laptop computer, a landline telephone, handheld computer, a tablet computer, a mobile phone, a media player, a personal digital assistant (PDA), or the like, including a combination of two or more of these items. It should be appreciated that the device 100 is only one example of an electronic device 100, and that the device 100 may have more or fewer components than shown, or a different configuration of components. The various components shown in FIG. 1 may be implemented in hardware, software or a combination of both hardware and software, including one or more signal processing and/or application specific integrated circuits.

The memory 102 may include high speed random access memory and may also include non-volatile memory, such as one or more magnetic disk storage devices, flash memory devices, or other non-volatile solid state memory devices. In some embodiments, the memory 102 may further include storage remotely located from the one or more processors 106, for instance network attached storage accessed via the RF circuitry 112 or external port 148 and a communications network (not shown) such as the Internet, intranet(s), Local Area Networks (LANs), Wide Local Area Networks (WLANs), Storage Area Networks (SANs) and the like, or any suitable combination thereof. Access to the memory 102 by other components of the device 100, such as the CPU 106 and the peripherals interface 108, may be controlled by the memory controller 104.

The peripherals interface 108 couples the input and output peripherals of the device to the CPU 106 and the memory 102. The one or more processors 106 run various software programs and/or sets of instructions stored in the memory 102 to perform various functions for the device 100 and to process data.

In some embodiments, the peripherals interface 108, the CPU 106, and the memory controller 104 may be implemented on a single chip, such as a chip 111. In some other embodiments, they may be implemented on separate chips.

The RF (radio frequency) circuitry 112 receives and sends electromagnetic waves. The RF circuitry 112 converts electrical signals to/from electromagnetic waves and communicates with communications networks and other communications devices via the electromagnetic waves. The RF circuitry 112 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry 112 may communicate with the networks, such as the Internet, also referred to as the World Wide Web (WWW), an Intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Long Term Evolution (LTE/4G). Global System for Mobile Communications (GSM), Enhanced Data GSM Environment (EDGE), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email, instant messaging, Short Message Service (SMS) and/or Multimedia Messaging Service (MMS)), or any other suitable communication protocol, including communication protocols not yet developed as of the filing date of this document.

The audio circuitry 114, the speaker 116, and the microphone 118 provide an audio interface between a user and the device 100. The audio circuitry 114 receives audio data from the peripherals interface 108, converts the audio data to an electrical signal, and transmits the electrical signal to the speaker 116. The speaker converts the electrical signal to human-audible sound waves. The audio circuitry 114 also receives electrical signals converted by the microphone 116 from sound waves. The audio circuitry 114 converts the electrical signal to audio data and transmits the audio data to the peripherals interface 108 for processing. Audio data may be may be retrieved from and/or transmitted to the memory 102 and/or the RF circuitry 112 by the peripherals interface 108. In some embodiments, the audio circuitry 114 also includes a headset jack (not shown). The headset jack provides an interface between the audio circuitry 114 and removable audio input/output peripherals, such as output-only headphones or a headset with both output (headphone for one or both ears) and input (microphone).

The I/O subsystem 120 provides the interface between input/output peripherals on the device 100, such as the touch screen 126 and other input/control devices or components, such as device-control sensors 128, and the peripherals interface 108. The I/O subsystem 120 includes a touch-screen controller 122 and one or more input controllers 124 for other input or control devices. The one or more input controllers 124 receive/send electrical signals from/to other input or control devices 128. The other input/control devices 128 may include physical buttons (e.g., push buttons, rocker buttons, etc.), dials, slider switches, sticks, and so forth.

The touch screen 126 provides both an output interface and an input interface between the device and a user. The touch-screen controller 122 receives/sends electrical signals from/to the touch screen 126. The touch screen 126 displays visual output to the user. The visual output may include text, graphics, video, and any combination thereof. Some or all of the visual output may correspond to user-interface objects, further details of which are described below.

The touch screen 126 also accepts input from the user based on haptic and/or tactile contact. The touch screen 126 forms a touch-sensitive surface that accepts user input.

In some embodiments, in addition to the touch screen, the device 100 may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from the touch screen 126 or an extension of the touch-sensitive surface formed by the touch screen 126.

The device 100 also includes a power system 130 for powering the various components. The power system 130 may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the software components include an operating system 132, a communication module (or set of instructions) 134, a contact/motion module (or set of instructions) 138, a graphics module (or set of instructions) 140, a user interface state module (or set of instructions) 144, and one or more applications 146, including a VII Client 149 and an SST Client (as each term is defined below) 150.

The operating system 132 (e.g., Darwin, RTXC, LINUX, UNIX, OS X, iOS, ANDROID, WINDOWS, or an embedded operating system such as VxWorks) includes various software components and/or drivers for controlling and managing general system tasks (e.g., memory management, storage device control, power management, etc.) and facilitates communication between various hardware and software components.

The communication module 134 facilitates communication with other devices over one or more external ports 148 and also includes (i) various software components for handling data received by the RF circuitry 112 and/or the external port 148, and (ii) a device interface and client application that enable communications with Variable Identifier information (jointly herein, (a "VII Client") 149—as taught by the Related Inventions, in addition to and independently of email addresses, telephone numbers, social network or social media registration, or instant messaging handles, aliases or addresses. The external port 148 (e.g., Universal Serial Bus (USB), FIREWIRE, etc.) is adapted for coupling directly to other devices or indirectly over a network (e.g., the Internet, wireless LAN, etc.).

The contact/motion module 138 detects contact with the touch screen 126 or interaction with other input/control devices 100, in conjunction with the touch-screen controller 122. The contact/motion module 138 includes various software components for performing various operations related to detection of contact with the touch screen 122, such as determining if contact has occurred, determining if there is movement of the contact and tracking the movement across the touch screen, and determining if the contact has been broken (i.e., if the contact has ceased). Determining movement of the point of contact may include determining speed (magnitude), velocity (magnitude and direction), and/or an acceleration (including magnitude and/or direction) of the point of contact. In some embodiments, the contact/motion module 126 and the touch screen controller 122 also detects contact on the touchpad.

The graphics module 140 includes various known software components for rendering and displaying graphics on the touch screen 126. Note that the term "graphics" includes any object that can be displayed to a user, including without limitation text, web pages, icons (such as user-interface objects including soft keys), digital images, videos, animations and the like.

The device includes an application deploying sixth-sense technology (SST), known as the SST Client 150, which enables the discovery, alerting, and delivery of all forms (e.g., voice, video, data, multi-media) of global content and commerce among devices and people based on such sixth-sense communications capabilities.

The one or more applications 146 can include any applications installed on the device 100, including without limitation, a VII Client, an SST Client, a browser, address book, contact list, email, instant messaging, word processing, keyboard emulation, widgets, JAVA-enabled applications, encryption, digital rights management, voice recognition, voice replication, location determination capability (such as that provided by the global positioning system (GPS)), a music player (which plays back recorded music stored in one or more files, such as MP3 or AAC files), etc.

In some embodiments, the device may include a hardware GPS unit 151 which determines current location based on current GPS satellite locations and/or cell-tower positioning.

In some embodiments, the device 100 may include the functionality of an MP3 player, such as an iPod (trademark of Apple Computer, Inc.). In some embodiments, the device 100 is a device where operation of a predefined set of functions on the device is performed exclusively through the touch screen 126 and, if included on the device 100, the touchpad.

The predefined set of functions that are performed exclusively through the touch screen and the touchpad include navigation between user interfaces. In some embodiments, the touchpad, when touched by the user, navigates the device 100 to a main, home, or root menu from any user interface that may be displayed on the device 100. In such embodiments, the touchpad may be referred to as a "menu button." In some other embodiments, the menu button may be a physical push button or other physical input/control device instead of a touchpad.

User Attributes and User Profiles

The device 100 may have a single or plurality of user attributes and user profiles. These attributes and user profiles are created, set or maintained by each of one or more individuals using the device, or by the device itself applying an algorithm or other software program running on or deployed by the device (such individual, individuals or device creating, set or maintained the attributes or profile herein, a user) via the SST Client 150. User attributes may include, by way of example and not by way of limitation, one or more of the user's professional, associational, personal, physical, social, athletic, recreational, hobby, locational, geospatial, and other interests, preferences, and attributes, or any other data associated with the device or its user (collectively herein, "Attributes"). A user might set up one or more user profiles (each of which might contain or prioritize different attributes or topics) (herein, "Profiles"), such as a work profile, a hobby profile, a family profile, and a social profile. These Attributes and Profiles are stored in one or more databases that, using the SST Client 150, can be named, indexed, searched for, retrieved, edited, merged, grouped, terminated or otherwise configured by one or more users who have authorized access to the device and the specific SST Client.

One embodiment of the present SST invention relates to creating and providing people (herein, "seekers") with the ability to search, "sense" and be alerted to unknown third parties with whom they want or are willing to communicate ("recipients"), wherein both seekers and recipients are using devices equipped and operating both an SST Client and a VII Client—and engage directly in real-time communications with such unknown recipients, without knowing the identity, address, contact information or location of the recipients (herein, "unknown recipients").

Using features of an SST Client on the device 100, a user, or 'seeker', may search, detect, discover, alert and sense unknown recipients and their unknown devices with Attributes lying within specified parameters selected by the user of the first device—which Attributes of the at least one third-party device 200 might, but are not required to, overlap in whole or in part with the Attributes of the device 100 of the first user. The parameters might include, for example, third-party devices within one or more certain or general geographic location(s) or zone(s) (jointly herein, a "zone") being used by a person with a specified age range with a professional or academic interest in certain topics or fields.

Seekers can configure the SST Client on their device 100 to search for, identify, alert, and display when it has detected the searched-for attribute(s) and parameters of users, or 'recipient' of the at least one third-party device 200, and, using the VII Client 149 on each device, initiate contact and communications with such third party device, even when its traditional identification information is unknown.

Another embodiment creates and providers users, or seekers, with the ability to search, sense and be alerted to what other users (herein, a collaborator) are interested in, and/or with whom they want or are willing to communicate; and to connect those people in private (or public) and anonymous communications based on their shared interests and thoughts—where each device is equipped with and operating an SST Client and a VII Client.

For example, a collaborator might configure the SST Client on her device 100 to specify that she is interested in topics A, B and C; and is willing to communicate about topics B1 and C2 with other unknown seekers who are affiliated with the post-secondary academic community in a specified geographic region. That communication interest would be sensed by the SST Client on the device 200 of a third-party seeker with such an academic affiliation interested in communication topics B1 and C2, and trigger an alert on such device. Upon checking the alert and reading the related display, the seeker would use the SST Client on his device 200 to compose and send a private and anonymous email or other message to the collaborator, notifying her of his interest in communication topics B1 and C2. From there, the collaborator and seeker would engage in such further communications and exchange of information as they deem suitable; maintaining such privacy and anonymity as each desires, using the communications capabilities of the VII Client, as integrated with the SST Client.

A third embodiment relates to creating and providing participants, groups, businesses, organizations and other parties with the means to search, discover and be alerted to what other people are interested in, and to deliver, share and learn to, with and from new and unknown recipients, through the exchange of voice, video, data and multi-media.

For example, the product manager (herein, a seeker) of a major snowboard brand might want to learn what new tricks riders are trying in diverse urban and backwoods environments, and product enhancements and new performance criteria suggested by rider usage. Random riders (each, a responder) might configure the SST Client on his device 100 to specify that she is interested in snowboarding, and is willing to communicate about new tricks, urban riding, and extreme terrain with unknown persons and businesses interested in snowboarding. That communication interest would be sensed by the SST Client on the device 200 of the seeker, and trigger an alert on such device. Upon checking the alert and reading the related display, the seeker would use the SST Client on his device 200 to compose and send a private and anonymous email or other message to the responder, notifying him of his interest in new snowboarding tricks, urban riding, and extreme terrain. From there, responder and seeker would engage in such further communications and exchange of information as they deem suitable, such as the responder sending the seeker a secure link to a private video of his extreme rides down urban sidewalk steps and down gnarly mountain chutes; maintaining such privacy and anonymity as each desires, using the communications capabilities of the VII Client, as integrated with the SST Client.

Another example of this embodiment is where a person (user 1) desires to find out what interests others (user 2 et seq), inclusive of everyone from the newcomer at school, the person across town, or someone halfway around the globe. Using devices 100/200 equipped with and operating an SST Client and a VII Client, each of user 1 and user 2 configure their STT Client selecting to disclose to the public at large certain attributes. The device 100 of user 1 discovers such attributes of User 2, and displays them on user 1's device. User 1 thus gets a sense of and be alerted to the other guy's 'story', and be able to share voice, pictures, video and data content based on common interests, creating ties that bind, and bringing people together.

A fourth embodiment—illustrating the push operation of the SST Client—relates to creating and providing people with the ability to send real-time content to one or more others who might be interested in a particular topic.

An example of this embodiment is where a person or organization (herein, a 'broadcaster') wants to direct in real-time content (e.g., in the form of a message or voice alert) to one or more others ("recipients") who might be interested in a particular political or social cause. The device (or communications network) of both broadcaster and recipient would be equipped with and running an SST Client and VII Client. A Broadcaster can configure the SST Client on their device 100 to search for, identify, alert, and display specific attribute(s) and parameters in third-party devices. Others users of such third party devices 200/300 would configure their respective SST Client indicating various interests that they have and any time/place restrictions on communications with others regarding such interests. The device of the broadcaster discovers those people and groups who are interested in receiving the searched-for content, displays an alert when it has detected the searched-for attribute(s) and parameters of recipient(s) using at least one third-party device 200, and, using the VII Client 149 on each device, initiates contact and communications with such third party device, and then send the desired content, privately and anonymously, to all unknown recipients chosen by the broadcaster.

Another embodiment—illustrating the pull operation of our sixth-sense discovery invention—relates to creating and providing people with the ability to learn more about a particular topic.

An example of this embodiment is where a person (a seeker) wants to learn more about "gay marriage". She configures the SST Client on her device 100 to indicate that one of her interests is gay marriage, and a willingness to communicate with unknown third parties during business hours or when she is away from home. Separately, a prominent gay rights activist (an Activist) has configured the SST Client on his device 200 with comparable settings, together with his official role with a national human rights organization. Both devices are equipped with a VII Client. While attending a business conference, the seeker's device 100 senses that the device 200 of the Activist is nearby, and displays an alert. The seeker checks her device; learns that the national corporate spokesperson for The Human Rights Campaign (THRC), is sitting across the aisle; and using the VII Client 149 on each device, sends a text, privately and anonymously, to the Activist, seeking to set up an inquiry or even a meet and greet.

Without exchanging or revealing email addresses, phone numbers or other contact data, the seeker and Activist are able to exchange messages, and then, the Activist arranges for THRC to send seeker a full report reviewing both sides of the gay marriage debate.

A sixth embodiment relates to creating and providing businesses and people, and governments, institutions, and other organizations, with:

new methods for searching and prospecting for new customers or contacts, new methods for distributing and selling new and additional products to existing and new customers, new methods for engaging in any or all forms of commercial transactions, including without limitation sharing, sending, receiving, procuring, distributing, streaming, purchasing, subscribing, leasing, renting, borrowing, licensing, selling, or transmitting products, services or content (all such commercial transactions collectively, "Commercial Sale"), new methods for conducting market research, consumer surveys, surveys and focus groups for new product features, new products, product development, and research and development, new methods for forecasting demand and creating, maintaining and improving operations and supply-chain management, and new methods for conducting global, supra-national, national, regional and census, public health and other data-gathering; public policy development; dissemination of emergency alerts, public-health news and other information; distribution of benefits; and political outreach, recruitment, opinion polls, advocacy and other political activities.

An example of this embodiment is where a businesses or organization (a business) wants to discover and become aware of, and direct marketing content to, new customers and prospects (jointly, a consumer) for their products, services and causes. The business equips its customer-facing staff with tablets 100 running an SST Client and VII Client. Each staff member configures their SST Client identifying their expertise in specific categories of business products; ability to speak one or more languages; availability to engage in consumer communications during various intervals throughout the day. Separately, consumers holding devices 200/300 running SST and VII Clients configure their SST Client noting their interest in certain product categories, and their desire to text or call in Spanish at specified times of day or when present in certain locations (e.g., at home, in-store, or near-store). A Spanish-speaking business staff member with relevant product knowledge receives an alert on his device 100 of such consumer's interest, and is able, using the VII Client on his device, initiate a private and anonymous communication with such consumer, and then, at the consumer's convenience and regardless of location, renew the private and anonymous communication with the consumer, through and including the close of the sale. Using this embodiment, businesses will be able to sell direct to the public, without having to incur distribution costs, for example to distributors and retailers, or to digital distributors (e.g., Amazon).

Another example of this embodiment is where a media content producer (a producer) wants to discover and become aware of which groups of anonymous consumers (a viewer) are or might be interested in their content. The producer equips its server 100 running an SST Client and VII Client, and configures their SST Client listing and indexing their library of movies, videos and ads, along with other information such as duration, language, and pertinent pricing (if any). Separately, viewers holding devices 200/300 running SST and VII Clients configure their SST Client noting their interest in certain movie genres, video categories, and ad topics, along with any pertinent time and location parameters restricting when and where they are willing to receive and view such content. The producer's server 100 receives notice of such viewer's interest, and is able, using the VII Client on the server, establish a private and anonymous communication with such viewer, informing her that the content is available for purchase, streaming or download; and then complete the delivery of desired content to the anonymous viewer in a private communication.

A seventh embodiment relates to creating and providing consumers with new methods for purchasing products or services.

An example of this embodiment is where an individual (a driver) wants to remain anonymous throughout the entire process of purchasing a car, from research and screening, to referrals and recommendations, to closing the deal. Using a smartphone device 100, the driver configures the SST Client to indicate his interest in buying a new or used car with various attributes and that is available for inspection, test drive and delivery within a designated mileage radius from his place of work. Separately, car dealers, car-search platforms (e.g., Autotrader), and private sellers (jointly, sellers) configure the SST Clients on their computers 200 identifying the attributes (including, e.g., pictures and videos) of their inventory of cars for sale; while car-service organizations (e.g., CarFax; Consumer Reports magazine; Car & Driver magazine; state vehicle registration bureaus)(jointly, resource groups) configure the SST Clients on their servers 300 to provide access to car reviews, car specifications, and vehicle information. The driver's phone 100 discovers from sellers' computers 200 (using SST and VII Clients) car(s) meeting the driver's criteria and any pertinent available reviews, etc from resource groups, and displays an alert on his phone. When he taps on the alert, the SST Client opens and displays links to the sellers' car listings and resource groups' car reviews, etc. From there, the driver and sellers and/or resource groups would engage in such further communications and exchange of information as they deem suitable; maintaining such privacy and anonymity as each desires, using the communications capabilities of the VII Client, as integrated with the SST Client.

Another example of our searching, sensing, discovery, alerting, and delivery method for purchasing a product or service is where an inexperienced individual (a listener) wants to start a reggae musical collection. She configures the SST client on her tablet or MP3 player 100 to indicate her reggae interest and solicit names of top reggae performers, critics and bloggers. Separately, at least one reggae performer, critic or blogger (a specialist) configures the SST Client on each of his computer 200 and music-storage server 300 identifying: (i) attributes both of reggae music (including any accompanying recommendation and referrals) stored on the server and referencing playlists of various collections comprised of single and multiple artists for first-time reggae followers, and of persons with whom they are willing to consult (while preserving the privacy of their contact information); and any personal temporal, location and other parameters restrictions on the devices that might sense and communicate with such specialist. The listener's device 100 discovers from specialist's computer 200 and server 300 (using SST and VII Clients) music and any recommendations or referrals meeting the listener's criteria and displays an alert on her phone. When she taps on the alert, the SST Client opens and displays links to the specialist. From there, the listener and specialist would engage in such further communications and exchange of information as they deem suitable; maintaining such privacy and anonymity as each desires, using the communications capabilities of the VII Client, as integrated with the SST Client.

In an eighth embodiment, a user (an initiator) can selectively communicate about desired topics with known or unknown people (a recipient) possessing certain characteristics who are using one or more other devices whose identification information is unknown. Using device 100 configured with an SST Client, the initiator launches the SST Client, and identifies an attribute or any other data associated with the device or its user, that he wants to make known to other devices and users whose identification is unknown, which attribute is compiled by the SST Client; the VII Client on the first device 100 enables communication with other devices 200 (also deploying a VII Client) whose identification information is unknown; the SST Client on the first device searches for and identifies at least one criterion (such as attribute, location, time of day, date, etc) for sharing such attribute with at least one other user or device deploying an SST Client, which criterion is compiled by the first SST Client; the SST Client running on the first device identifies and locates other devices based on such one or more criteria; obtains information regarding the other devices meeting such criteria; compiles the information regarding the other devices meeting such criteria to enable selection of at least one device to initiate communication using the VII Client on the first device; and displays a selection of the at least one device from the compiled information of the other devices meeting such criteria. Using the SST Client on the first device 100, the initiator selects the at least one other device 200 either with which he wants to communicate on a desired topic or which is being used by a person with the desired characteristics, and then using privacy preference settings within the SST Client on the first device 100, chooses whether he wants to preserve the privacy of his contact information; reveal his real name or location; or open a private 1:1 or public communication with such selected recipient or device 200; wherein the privacy preferences enable the device to provide variable identification information to the at least one other device; enables the VII Client on the first device to specify whether the Variable Identifier is associated with private content, wherein the private content is sent only to the at least one other device; and sends the private content from the first device to the at least one other device.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

We claim:

1. A method for communicating beyond fixed known endpoints, that enables searching, detecting, sensing, and discovering attributes, characteristics, parameters or other data among known and unknown devices and their users, authenticating such devices and their users, message routing and directing private or anonymous targeted communications to and with specific devices and their users, and maintaining continuous or initiating repeat communications with and to such specific devices and their users, in each case regardless of initial or continued location of such devices or the proximity of such devices in a limited or designated physical area or zone, the method comprising:

launching a client application (herein, a sixth-sense client, or "SS Client") on a first device, which enables searching, detecting, sensing, or discovering (collectively or separately, 'discovering') attributes, characteristics, interests, preferences, parameters, location (collectively or separately, 'attributes') associated with other recipient devices or the users of such recipient devices;

setting the SS Client on the first device to:
(i) discover the attributes (searched-for attributes) of one or more recipient devices or their users;
(ii) communicate with other devices whose identification information is unknown; and
(iii) locate other devices (screened devices') worldwide or within one or more certain or general geographic location(s) or zone(s) (jointly herein, a "zone");

prompting the SST Client on the first device to obtain and compile on the first device:
(i) information or data from the screened devices (compiled data') consisting of one or more of the searched-for attributes associated with the device (including its software or firmware) or its users; and
(ii) unique device identification information, vendor or advertising IDs, or other device identifying information specific to each screened device (jointly herein, "device identifying information", or "DII");

applying one or more filters on the first device to analyze such compiled data or DII to enable the selection of least one screened device (a 'designated screened device'; and the compiled data or DII used to enable such selection herein, 'variable identification information', or "VII");

enabling privacy preferences for the first device, wherein the privacy preferences enable the first device to send VII of the first device to a designated screened device;

enabling the SST Client on the first device to specify whether a service message is a private service message, wherein the private service message is sent only to, and is accessible only by, the designated screened device;

using VII of the designated screened device for authentication, sending the service message only to the specific designated screened device (herein, the 'recipient device'), where either of the following conditions is also satisfied:
(a) the contact information (e.g., email address; public or private cryptography key; IM screen name; social media or Internet screen name, handle, alias, or avatar; phone number; MAC address; IP address) (collectively herein "Contact Information") of the recipient device is not previously known to any of: the first device, its users, or any business, social or communications network to which the first device or any of its users is a member; or
(b) the service message is authenticated by or from the first device using such variable identification information, and without using email, public or private cryptography key, instant messaging (IM), text messaging, telephony or any other communications protocol or technique based on fixed endpoints where any of such Contact Information is known to any of: the first device, any of its users, or any business, social or communications network of which the first device or any of its users is a member; and enabling the SS Client on a recipient device to authenticate, using the VII of the first device, the identity of the first device and to initiate or maintain communications by the recipient device with the first device, regardless of whether either device remains in the in the zone in which initial contact and authentication between the devices was established.

2. The method of claim 1, further comprising:
detecting, at the SS Client on the first device, a search by the SS Client on a recipient device; and
sending compiled data from the SS Client on the first device to the SS Client on a recipient device, including identification of one or more attributes searched for by the SS Client on the second device.

3. The method of claim 1, further comprising:
setting the SS Client on the first device and using VII on each of the first device and one or more of the recipient devices to authenticate and communicate with the recipient devices, to discover stories, topics, interests, preferences or other content (collectively, Stories) associated with one or more of the recipient devices or their users;
setting the SS Client on the first device and using VII on each of the first device and the recipient devices to authenticate and communicate with one or more of the recipient devices, to discover content, products, goods, services, information or other data - in any medium or format (collectively, Content)—whose commercial sale is being searched, offered, or identified as being of interest or potential interest (such Content, 'Topical Content') to one or more of the recipient devices or their users;
setting the SS Client on the first device and using VII on each of the first device and or the recipient devices to authenticate and communicate with the recipient devices, to alert, display, notify, evaluate, screen, compare or prioritize searched-for attributes, Stories, Content or Topical Content (collectively, "searched-for Interests") associated with one or more of the recipient devices or their users;
the SS Client on the first device and using VII on each of the first device and one or more of the recipient devices to authenticate and communicate with the recipient devices, for the commercial sale of searched-for Interests by, between or among one or more of the recipient devices or their users;
setting the SS Client on the first device and using VII on each of the first device and one or more of the recipient devices to authenticate and communicate with the recipient devices, to market, advertise, deliver product information and other marketing content, solicit and engage to or with one or more recipient devices, or the users of such devices, based on searched-for Interests associated with such devices, or the users of such devices; or
setting the SS Client on the first device and using VII on each of the first device and one or more of the recipient devices to authenticate and communicate with the recipient devices, to educate, inform, persuade, lobby, advocate, engage or otherwise transmit information or other data to or with one or more of the recipient devices or their users, based on searched-for Interests associated with the recipient devices or their users.

4. The method of claim 1, further comprising using VII on each of the first device and one or more of the recipient devices to authenticate and communicate with the recipient devices, for the first device to communicate with the recipient devices when specified, at the option of the first device or one or more of the recipient devices, for use in lieu of email, public or private cryptography key, instant messaging (IM), text messaging, multimedia messaging, telephony, data transfer, video or music streaming, or any other communications protocol or technique based on fixed endpoints.

5. A method for communicating beyond fixed known endpoints, that enables marketing, advertising, delivering product information or other marketing content, soliciting and engaging to and with one or more known or unknown devices or their user(s); authenticating such devices and their users; routing messages, and direct private or anonymous targeted communications, to and with specific devices and their users; and maintaining continuous or initiating repeat communications with and to such specific devices and their users; in each case regardless of initial or continued location of such devices or the proximity of such devices in a limited or designated physical area or zone, the method comprising:
launching a client application (herein, a sixth-sense client or, "SS Client") on a first device , wherein the client application enables searching, detecting, sensing, or discovering (collectively or separately, 'discovering') any one or more of the following:
(i) attributes, characteristics, interests, or preferences (collectively, attributes),
(ii) stories, topics, interests, or preferences (collectively, Stories),
(iii) content, products, goods, or services, (collectively, Content), or
(iv) Content of a commercial sale of which is being searched, offered, or identified as being of interest or potential interest (such Content, 'Topical Content') to one or more devices (recipient devices) or the user(s) of the recipient devices,
(such attributes, Stories, Content or Topical Content collectively, 'searched-for Interests' associated with one or more of other devices or the users of the other devices);
setting the SS Client on the first device to:
(i) discover the searched-for Interests of one or more of other devices or their users;
(ii) communicate with other devices whose identification information is unknown; and
(iii) locate other devices (jointly. 'screened devices') worldwide or within one or more certain or general geographic location(s) or zone(s) (jointly herein, a "zone");
prompting the SST Client on the first device to obtain and compile on the first device:
(i) information or data from the screened devices ('compiled data') consisting of one or more of the searched-for attributes associated with the device (including its software or firmware) or its users; and
(ii) unique device identification information, vendor or advertising IDs, or other device identifying information specific to each screened device (jointly herein, "device identifying information", or "DII");
applying one or more filters on the first device to analyze such compiled data or DII to enable the selection of least one screened device (a 'designated screened device';

and the compiled data or DII used to enable such selection herein, 'variable identification information', or "VII");

enabling privacy preferences for the first device, wherein the privacy preferences enable the first device to send VII of the first device to a designated screened device;

enabling the SST Client on the first device to specify whether a service message is a private service message, wherein the private service message is sent only to, and is accessible only by, the designated screened device;

using VII of the designated screened device for authentication, sending the service message only to the specific designated screened device (herein, the 'recipient device'), where either of the following conditions is also satisfied:
  (a) the contact information (e.g., email address; public or private cryptography key; IM screen name; social media or Internet screen name, handle, alias, or avatar; phone number; MAC address; IP address) (collectively herein "Contact Information") of the recipient device is not previously known to any of: the first device, its users, or any business, social or communications network to which the first device or any of its users is a member; or
  (b) the service message is authenticated by or from the first device using such variable identification information, and without using email, public or private cryptography key, instant messaging (IM), text messaging, telephony or any other communications protocol or technique based on fixed endpoints where any of such Contact Information is known to any of: the first device, any of its users, or any business, social or communications network of which the first device or any of its users is a member; and enabling the SS Client on a recipient device to authenticate, using the VII of the first device, the identity of the first device and to initiate or maintain communications by the recipient device with the first device, regardless of whether either device remains in the in the zone in which initial contact and authentication between the devices was established.

6. A method for communicating beyond fixed known endpoints, that enables commercial sales with, to or from one or more known or unknown devices or their users, authenticating such devices and their users, routing messages and directing private or anonymous targeted communications to and with specific devices and their users, and maintaining continuous or initiating repeat communications with and to such specific devices and their users, in each case regardless of initial or continued location of such devices or the proximity of such devices in a limited or designated physical area or zone, the method comprising:

launching a client application (herein, a sixth-sense client, or "SS Client") on a first device, wherein the client application enables searching, detecting, sensing, or discovering (collectively or separately, 'discovering') either
  (A) (i) content, products, goods, or services (collectively, 'content'),
      (ii) one or more categories or genres of Content (collectively, 'content types'), or
      (iii) interest in or preferences for content types, or
  (B) attributes, characteristics, interests, preferences, parameters or other data regarding or otherwise relating to the content or content types (collectively, 'content attributes'), (such content, content types, and content attributes collectively, 'searched-for Content' associated with the recipient devices, or the users of the recipient devices);

setting the SS Client on the first device to discover the searched-for Content of the recipient devices or their users; communicate with other devices whose identification information is unknown; and locate other devices (jointly, 'screened devices') worldwide or within one or more certain or general geographic location(s) or zone(s) (jointly herein, a "zone");

prompting the SST Client on the first device to obtain and compile on the first device:
  (i) information or data from the screened devices ('compiled data') consisting of one or more of the searched-for attributes associated with the device (including its software or firmware) or its users; and
  (ii) unique device identification information, vendor or advertising IDs, or other device identifying information specific to each screened device (jointly herein, "device identifying information", or "DII");

applying one or more filters on the first device to analyze such compiled data or DII to enable the selection of least one screened device (a 'designated screened device'; and the compiled data or DII used to enable such selection herein, 'variable identification information', or "VII");

enabling privacy preferences for the first device, wherein the privacy preferences enable the first device to send VII of the first device to a designated screened device;

enabling the SST Client on the first device to specify whether a service message is a private service message, wherein the private service message is sent only to, and is accessible only by, the designated screened device;

using VII of the designated screened device for authentication, sending the service message only to the specific designated screened device (herein, the 'recipient device'), where either of the following conditions is also satisfied:
  (a) the contact information (e.g., email address; public or private cryptography key; IM screen name; social media or Internet screen name, handle, alias, or avatar; phone number; MAC address; IP address) (collectively herein "Contact Information") of the recipient device is not previously known to any of: the first device, its users, or any business, social or communications network to which the first device or any of its users is a member; or
  (b) the service message is authenticated by or from the first device using such variable identification information, and without using email, public or private cryptography key, instant messaging (IM), text messaging, telephony or any other communications protocol or technique based on fixed endpoints where any of such Contact Information is known to any of: the first device, any of its users, or any business, social or communications network of which the first device or any of its users is a member; and enabling the SS Client on a recipient device to authenticate, using the VII of the first device, the identity of the first device and to initiate or maintain communications by the recipient device with the first device, regardless of whether either device remains in the in the zone in which initial contact and authentication between the devices was established.

* * * * *